United States Patent [19]

Winsel

[11] Patent Number: 5,407,555
[45] Date of Patent: Apr. 18, 1995

[54] HYDROGEN ROD ELECTRODE WITH INTEGRATED HYDROGEN SOURCE

[76] Inventor: August Winsel, Fasanenstrasse 8a, D-6233 Kelkheim/Taunus, Germany

[21] Appl. No.: 958,343

[22] PCT Filed: Mar. 18, 1992

[86] PCT No.: PCT/EP92/00597

§ 371 Date: Feb. 18, 1993

§ 102(e) Date: Feb. 18, 1993

[87] PCT Pub. No.: WO92/18858

PCT Pub. Date: Oct. 29, 1992

Related U.S. Application Data

[63] Continuation-in-part of Ser. No. 727,877, Jul. 10, 1991, Pat. No. 5,242,565.

[30] Foreign Application Priority Data

Apr. 19, 1991 [DE] Germany ............... 41 12 784.6

[51] Int. Cl.6 ............................................. G01N 27/26
[52] U.S. Cl. ..................................... 204/435; 204/433
[58] Field of Search ............... 204/433, 435, 292, 293; 429/12, 30, 41, 42, 72, 192, 229, 218

[56] References Cited

U.S. PATENT DOCUMENTS

| | | | |
|---|---|---|---|
| 3,201,282 | 8/1965 | Justi et al. ................. | 136/86 |
| 3,622,397 | 11/1971 | Belove ....................... | 136/178 |
| 3,976,502 | 8/1976 | Sekido et al. ............... | 136/6 GC |
| 4,105,330 | 8/1978 | Kordesch ................... | 429/27 |
| 4,189,526 | 2/1980 | Cretzmeyer et al. ........ | 429/13 |
| 4,402,817 | 9/1983 | Maget ....................... | 204/301 |
| 4,489,141 | 12/1984 | Stafford et al. .............. | 429/23 |
| 4,556,612 | 12/1985 | Thibault et al. ............. | 429/54 |
| 4,800,139 | 1/1989 | Kenjyo ...................... | 429/42 |
| 4,808,292 | 2/1989 | Kessler et al. ............... | 204/435 |
| 5,043,234 | 8/1991 | Tomantschger et al. ..... | 429/59 |
| 5,143,799 | 8/1992 | Tsenter ...................... | 429/229 |

FOREIGN PATENT DOCUMENTS

| | | |
|---|---|---|
| 961420 | 1/1975 | Canada . |
| 0144002 | 6/1985 | European Pat. Off. . |
| 1164525 | 3/1964 | Germany . |
| 1496247 | 3/1969 | Germany . |
| 1542565 | 10/1970 | Germany . |
| 1673284 | 8/1971 | Germany . |
| 2139771 | 2/1973 | Germany . |
| 3342969 | 6/1985 | Germany . |
| 3532335 | 3/1987 | Germany . |
| 3702138 | 8/1988 | Germany . |
| 394640 | 12/1965 | Switzerland . |

OTHER PUBLICATIONS

E. Justi and A. Winsel, "Cold Combustion Fuel Cells", Brennstoffzellen (Fuel Cells), Steiner-Verlag, Weisbaden, 1962 (pp. 69 to 74).

*Primary Examiner*—John Niebling
*Assistant Examiner*—Bruce F. Bell
*Attorney, Agent, or Firm*—Weiser & Associates

[57] ABSTRACT

A hydrogen rod electrode including a hydrogen electrode in one aperture of a gas tube, which is connected at the other aperture to a cell holder for containing a hydrogen generation cell. This is used as a reference electrode for electrochemical measurements or as a pH measuring electrode. Through an electric circuit, which is also integrated, hydrogen is provided in adequate quantities for the operation concerned.

44 Claims, 2 Drawing Sheets

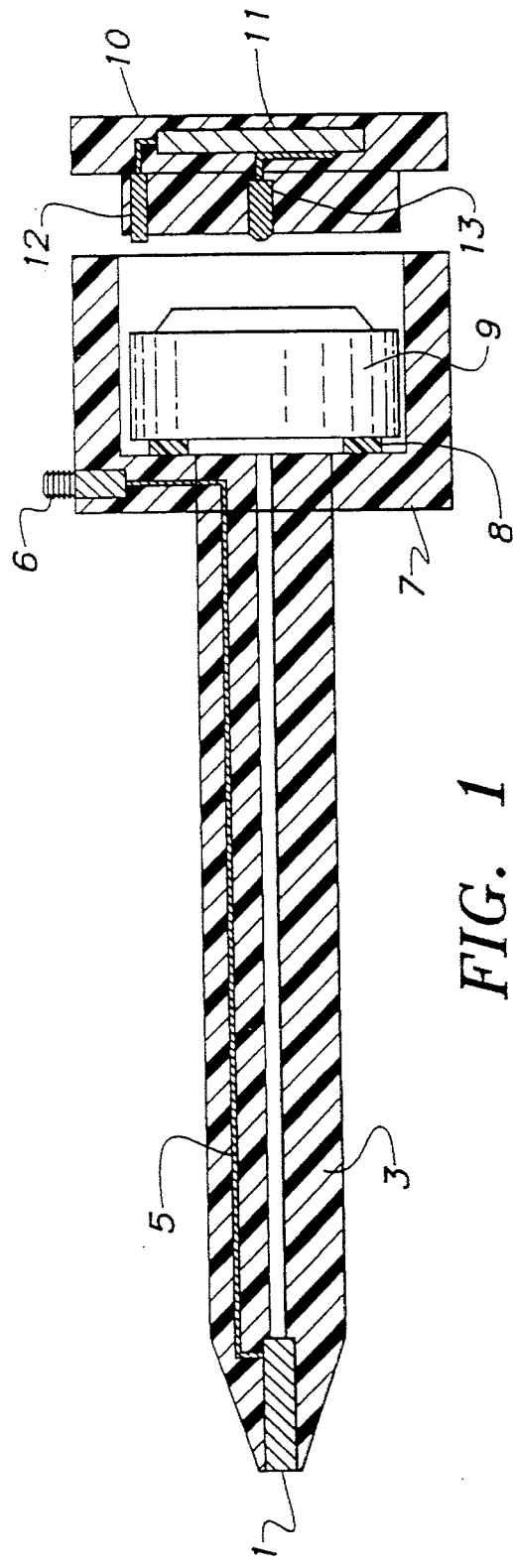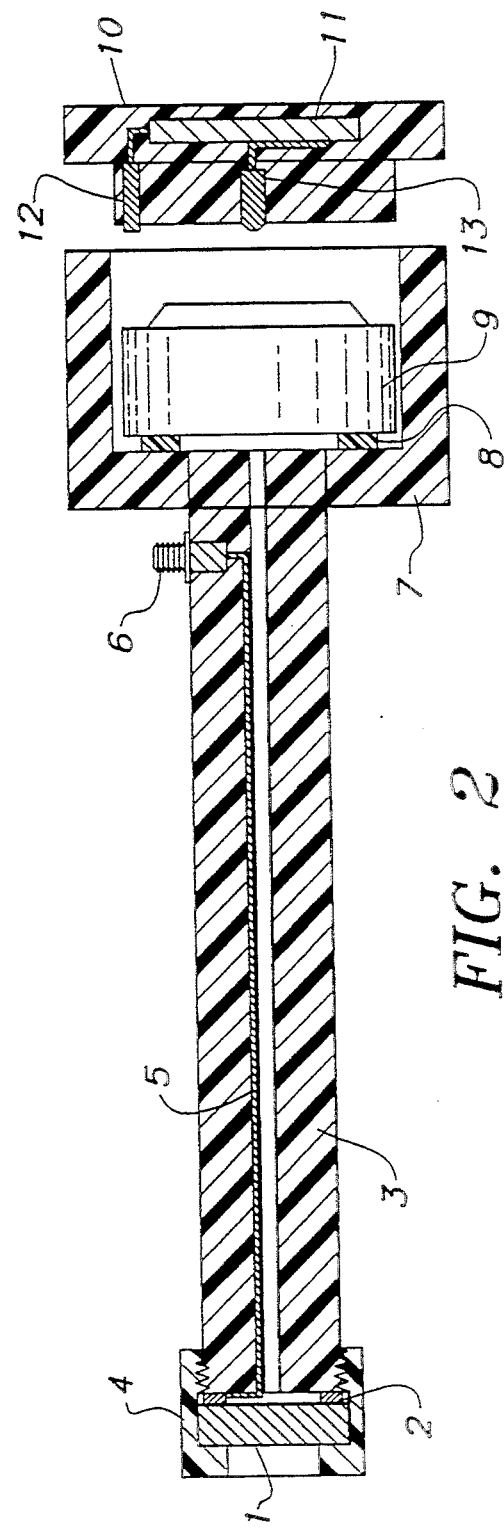

HYDROGEN ROD ELECTRODE WITH INTEGRATED HYDROGEN SOURCE

RELATED CASE

This is a continuation-in-part of prior U.S. patent application Ser. No. 07/727,877, filed Jul. 10, 1991, now U.S. Pat. No. 5,242,565 and entitled DEVICE FOR ELECTROCHEMICAL GENERATION OF GASES FOR THE TRANSPORTATION OF FLUIDS AND SIMILAR MEDIUMS.

BACKGROUND OF THE INVENTION

The invention pertains to a hydrogen electrode in rod form, especially for use as a reference electrode in electrochemical measurements or as a pH measuring electrode, which contains the integrated hydrogen supply in the form of a hydrogen generation cell of the type described in DE-PS 35 32 335 and makes it available during operation in an amount adequate for the given function.

DE-PS 35 32 335 discloses an electrochemical cell for generating hydrogen and/or oxygen which is generally comprised of an anode, a cathode and an aqueous electrolyte in a metal and/or plastic housing. The anode is composed of a substance subject only to electrochemical oxidation in its initial state. The cathode is either a hydrogen releasing electrode, or is composed of an electrochemically reducible substance. The cell contains an oxygen releasing electrode, and either hydrogen or oxygen can be formed responsive to a flow of current. The applied current results in a flow of gas from the pores of what essentially constitutes a gas diffusion electrode, which functions either as a cathode or as an anode, and is permitted to pass to the outside of the cell through the pores of a hydrophobic diffusion membrane. A preferred gas generating cell includes a metal (preferably zinc) anode, a hydrogen cathode composed of a layer of metal and/or carbon powder with a PTFE binder on a metal mesh, laminated with a porous PTFE film, and an alkaline electrolyte. The cell can be used to produce either hydrogen or oxygen in amounts proportional to the current which is applied.

The hydrogen electrode is of central importance in electrochemical measuring technology. This is apparent from the so-called pH value, i.e., the negative of the hydrogen ion exponent. It is obtained by taking the common logarithm of the concentration (or the activity) of the hydrogen ions in a solution. This is the most commonly used quantity for characterizing aqueous solutions.

The measurement is generally performed by immersing a platinized platinum foil into the solution and causing hydrogen to flow around it. It then represents one potential pole of a measuring cell, whose other pole is a reference electrode of the same or different type in a standard solution of known pH, which is galvanically connected with the test solution by an electrolytic switch.

The hydrogen electrode is used even more commonly as an unloaded reference electrode in electrochemical measuring cells. In this case, the hydrogen-covered platinum electrode is immersed in a so-called Luggin capillary, whose opening is located directly in front of the test electrode, with which the unloaded reference electrode forms a galvanic cell. The potential changes of the galvanic cell are due solely to the potential changes of the test electrode during current flow or otherwise changing test conditions.

SUMMARY OF THE INVENTION

Hydrogen electrodes have the serious disadvantage that they require a source of hydrogen in the form of a compressed-gas cylinder with valves and tubes. This makes them expensive and difficult to handle. A new type of hydrogen supply technique would make it much easier to use hydrogen electrodes. This problem is solved by the rod electrode in accordance with the present invention. It comprises three basic parts: a preferably exchangeable hydrogen electrode, a hydrogen tube and an exchangeable hydrogen generation cell as the source of the hydrogen. The arrangement of the apparatus and the method of operation of the invention are explained below with reference to the following illustrations.

BRIEF DESCRIPTION OF THE DRAWINGS

FIG. 1 is a cross-sectional view of a hydrogen rod electrode of the present invention.

FIG. 2 is a cross-sectional view of a first alternative embodiment of the hydrogen rod electrode of the present invention.

In these several views, like reference numbers denote similar structure.

DETAILED DESCRIPTION OF PREFERRED EMBODIMENTS

Figures 3, 4:
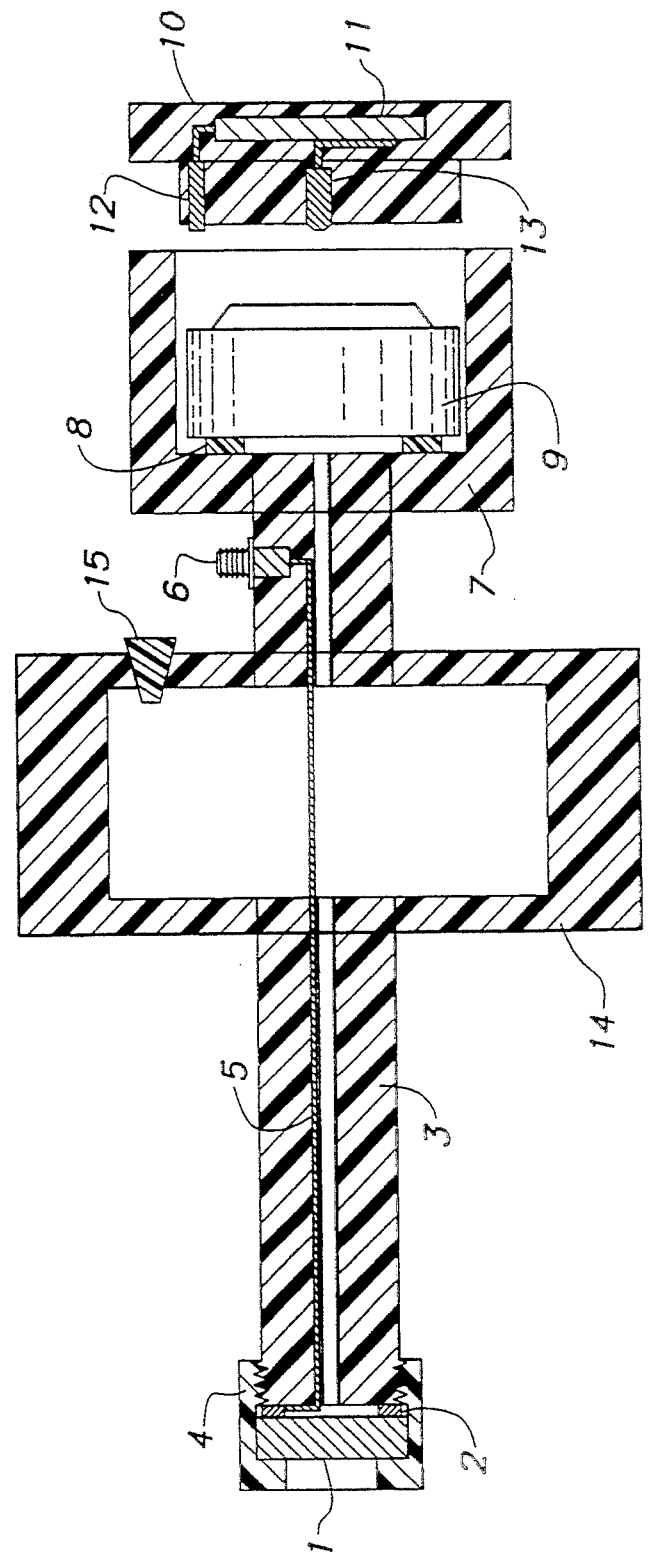
FIG. 3 is an elevational view of an alternative embodiment terminal for use with the hydrogen rod electrode of the present invention.
FIG. 4 is a cross-sectional view of a second alternative embodiment of the hydrogen rod electrode of the present invention, which incorporates a reservoir for a reference solution.

FIG. 1 shows the hydrogen electrode (1), which consists of a platinized platinum wire, which is located in the tapered opening of a hydrogen tube (3). The other end of the hydrogen tube is screwed, plugged or cemented into the actual gas cell casing (7) so that the connection is gas-tight. This preferably cylindrical gas cell casing (7) holds the hydrogen generation cell (9) specified in DE-PS 35 32 335 (which is formed as a button cell having a housing for receiving an electrolyte containing zinc gel, a compressible body for receiving additional electrolyte, an electrolyte-soaked fleece, a separator, a support ring and a gas diffusion electrode which is preferably formed as a PTFE-bonded Raney nickel powder rolled into a nickel mesh).

The hydrogen generating cell (9) contains zinc powder or zinc gel and potassium hydroxide as well as the so-called hydrogen generation electrode. In the hydrogen generation electrode, a catalyst layer bound with PTFE is rolled into a metal mesh and is covered with a fine-pored PTFE foil on the side away from the zinc. The zinc electrode and the hydrogen generation electrode are located in a housing that usually comprises two metal parts insulated from each other, one of which is connected with the zinc electrode, while the other is connected with the hydrogen generation electrode to allow electron conduction. The housing part containing the hydrogen generation electrode communicates with the interior of the gas tube (3) through at least one drill hole. The drill hole can be sealed by a sticker, which releases the hole during operation of the cell due to the overpressure.

The gas cell casing (7) is closed by the screw-on or snap-on cap (10), which can perform a number of functions. For example, after the cell has been closed, it is useful for the cap to exert pressure on the cell (9) by means of elastic spring elements (not shown), so that the cell communicates with the gas tube (3) through the above-mentioned drill hole in the cell housing part by means of the annular gasket (8). These spring elements can be the electronic contacts (12) and (13), which contact the two parts of the housing. It is also useful for the cap (10) to carry a fixed or variable electrical resistor (11) in series to an on-off switch, with which the contacts (12) and (13) are connected. For example, this can be a potentiometer (11) with an "off position." Instead of being connected with the cap, this electrical switching and current-regulating circuit can also be permanently connected with the gas cell casing (7).

To avoid disturbances by foreign gases, a metal wire (5) is preferably led from the hydrogen electrode to the gas cell casing inside the hydrogen tube or embedded in its wall. The wire terminates in a contact screw (6) that is accessible from the outside or in a single-pole socket (16), as shown in FIG. 3.

Platinum electrodes are especially suitable for use in acid media, because they are also resistant to all oxidizing acids in these media. However, many other metals of Group VIII of the Periodic Table of Elements, their alloys, or electron-conducting solids metallized with these metals or alloys are suitable for use, provided that they have the catalytic capacity for chemisorptive cleavage of the hydrogen molecule. This is true, e.g., of palladium and iridium, as well as activated carbon metallized (catalyzed) with these metals. In this regard, black coatings of large surface area are especially effective.

In alkaline and neutral solution, nickel is a very effective hydrogen catalyst, especially in the form of Raney nickel. This is a powdered material obtained from a nickel/aluminum alloy by extraction of the aluminum with an alkali hydroxide. Hydrogen electrode materials can be produced from it by power-metallurgical production methods. Methods of this type are described in E. Justi and A. Winzel: Brennstoffzellen [Fuel Cells], Steiner-Verlag, Wiesbaden, 1962, and in patents cited in this book. However, electrodes suitable for this purpose can also be produced from the catalyst powders by thoroughly mixing them with PTFE powder in very high-speed blade mills and then rolling them into a metal grid made of nickel, silver, gold or even titanium. Electrodes of this type are also commonly provided with a fine-pored, hydrophobic PTFE layer on one side, which is turned towards the reacting gas and keeps the electrode/electrolyte/gas three-phase boundary stable. Electrode structures of this type are described in EP-PS 144 002 (1983). However, it can be advantageous to improve the storage capacity by using so-called hydride storage alloys in addition to Raney nickel (DE-OS 37 02 138 [1987]).

FIG. 2 shows how a porous hydrogen electrode of this type can be integrated in the rod electrode of the invention. (1) designates the body of the electrode, which is screwed onto the end of the hydrogen tube (3) by a screw cap (4). An electrical contact disk (2) is located between them, and is connected with a contact screw (6) by the contact wire (5). The contact screw is fastened to the hydrogen tube (3). The rod electrode in FIG. 2 is intended for insertion into a Luggin capillary. The screw part (4) can also be designed towards the front as a capillary opening. However, it can also hold an electrolytic switch in the form of a diaphragm, a swelling membrane or a semipermeable glass window, with which the electrolyte solution in the rod electrode is bounded from the external "test solution."

In some cases, the hydrogen tube (3) can be provided, in the region above the electrode (1), with a very fine drill hole, which is also immersed in the electrolyte in the test cell. It acts as a pressure-limiting valve by virtue of its capillary pressure. In most cases, however, it is sufficient to adjust the hydrogen supply in such a way that a small bubble occasionally escapes from the opening of the gas tube and into the electrolyte through the electrode (1).

For fast starting, the gas cell (9) is inserted in the mounting (7) without the paper sticker on the gas outlet opening. A large gas cell current is then turned on, with which, initially, the atmospheric oxygen in the gas tube is consumed by the gas cell (9). This causes electrolyte to be sucked into the hydrogen tube through the opening. This is followed by strong hydrogen generation, which blows out the hydrogen tube (3). Once this has occurred, the current and thus the hydrogen supply can be cut back to the minimal value. With economical consumption, measurements can be performed for more than a year. In this case, proper functioning can be checked by measuring the operating voltage that appears at the contacts (12) and (13). The contacts (12) and (13) are kept accessible from the outside for this purpose.

The presence of an adjustable or controllable hydrogen source inside the hydrogen rod electrode of the invention allows easier performance of pH measuring methods proposed earlier. For example, CH-PS 394,640 of 1962 (inventor: Dr. August Winsel) describes how the pores of a hydrogen electrode can be rinsed by surges of the test solution by utilizing both gravity and the overpressure of the gas to convey the test solution. DBP 1,164,525 of 1962 (inventor: Dr. August Winsel) also describes such a possibility. DBP 1,673,284 of 1967 (inventors: Dr. August Winsel and Dr. Rail Wendtland) claims a "process for the continuous pH measurement of liquids with a hydrogen diffusion electrode with a large-pored operating layer covered with fine-pored layers on both sides, such that the large-pored catalyst layer is filled with hydrogen gas, characterized by the fact that the hydrogen diffusion electrode, which is arranged between two electrolyte chambers, is continuously rinsed with the test liquid by a pressure difference between these chambers, and that the hydrogen pressure is continuously maintained during this process, and the pH value of this liquid is determined by the already well-known method of measuring the potential of the electrode." A similar procedure of pore flushing of hydrogen electrodes of the hydrophobic type is also described in DBP 1,496,247 of 1965 (inventor: Prof. Dr. August Winsel). The test liquid can be conveyed especially easily by exploiting the pressure energy of the hydrogen generated in the gas cell.

The possibility of continuous or discontinuous pore flushing is especially indicated when the hydrogen electrode is operated with a reference solution as the test solution, for example, a buffer solution (FIG. 4). The movement of the test liquid from an integrated reservoir (14) through the pores of the hydrogen electrode can also be effected by means of the integrated hydrogen generation cell, which supplies not only the hydrogen gas for the measuring operation, but also the necessary energy for conveying the test liquid. Since the test solution is saturated with the hydrogen gas due to the long contact time, the gas dissolved in the test solution is sufficient, in high-resistance measuring apparatus, for providing the test current in the hydrogen electrode. FIG. 4 shows an example of this operation of the invention in accordance with CH-PS 394,640. (15) designates the stopper of the reservoir (14). If one wishes to deliver the hydrogen gas from the gas cell (9) to the hydrogen electrode (1) parallel with and independent of the test solution, the two can be connected with one or more PTFE capillaries or with a porous sintered strip made of PTFE, into which the test solution from container (14) cannot penetrate due to its nonwettability. In general, the test solution and hydrogen gas can be conveyed side by side by a combination of a wettable structure (wick) and unwettable porous structure.

The combination of several hydrogen rod electrodes allows the performance of electrochemical measurements without any other, different reference electrodes. Thus, the pH can be determined when one rod electrode is immersed in the test solution and a second one is immersed in a reference solution, which is galvanically connected by well-known means with the test solution via an electrolytic switch. The voltage between the two is proportional to the difference of the pH values of the test solution and the reference solution.

Oxygen present in dissolved form in the test solution is reduced at the hydrogen electrode; this corresponds to an anodic load of the hydrogen electrode. The same applies to the reduction of oxidizing substances in the test solution, for example, nitrates and nitrites. Since different anodic loads are produced by applying different diffusion resistances in the electrolyte before two hydrogen electrodes, the concentration of oxidizable substance can be determined from the potential of two such electrodes. In this connection, it is easy to see that the two hydrogen electrodes can be mounted on one rod and can be supplied from a single hydrogen generation cell, but also that several gas cells connected in series or parallel can be used on one rod to supply the hydrogen electrodes and to transport the liquids.

I claim:

1. A hydrogen measurement electrode comprising a reference electrode, a gas generating cell for producing hydrogen for introduction to the reference electrode, and a conduit connecting the reference electrode and the gas generating cell, wherein the gas generating cell includes an anode, a cathode and an aqueous electrolyte in an enclosed cell housing, and wherein the cathode is formed of a hydrogen releasing substance.

2. The hydrogen measurement electrode of claim 1 wherein the reference electrode and the gas generating cell are remotely positioned relative to each other, and wherein the reference electrode and the gas generating cell are operatively connected only by the conduit so that hydrogen produced by the gas generating cell is supplied to the remotely positioned reference electrode.

3. The hydrogen measurement electrode of claim 2 wherein the reference electrode and the gas generating cell communicate with opposing ends of the conduit.

4. The hydrogen measurement electrode of claim 1 wherein the cathode is a hydrogen diffusing electrode for communicating with the conduit through a hydrophobic diffusion membrane.

5. The hydrogen measurement electrode of claim 4 wherein the cathode includes a catalyst layer bound with polytetrafluoroethylene and rolled into a metal mesh, and a porous polytetrafluoroethylene foil covering the catalyst layer and the metal mesh.

6. The hydrogen measurement electrode of claim 5 wherein the polytetrafluoroethylene foil lies on a side of the cathode which faces away from the anode.

7. The hydrogen measurement electrode of claim 5 wherein the anode is zinc.

8. The hydrogen measurement electrode of claim 7 wherein the electrolyte is potassium hydroxide.

9. The hydrogen measurement electrode of claim 1 which further includes means for electrically connecting the anode and the cathode.

10. The hydrogen measurement electrode of claim 9 wherein the connecting means is a resistor.

11. The hydrogen measurement electrode of claim 10 wherein the connecting means is a potentiometer.

12. The hydrogen measurement electrode of claim 1 wherein the reference electrode is formed of a material having a catalytic capacity for chemisorptive cleavage of hydrogen molecules selected from the group consisting of Group VIII metals of the Periodic Table of Elements, alloys of such metals, and electron-conducting solids metallized with such metals and alloys of such metals.

13. A hydrogen measurement electrode comprising:
a conduit having a first end for receiving an electrode body which serves as a reference electrode, and a second end opposing the first end for receiving a hydrogen generating cell having an anode and a cathode, for producing hydrogen for introduction to the reference electrode;
an electrical connection extending along the conduit for connecting the electrode body to a terminal for the hydrogen measurement electrode; and
means for electrically connecting the anode and the cathode of the hydrogen generating cell, for producing a flow of hydrogen from the hydrogen generating cell, along the conduit, to the electrode body.

14. The measurement electrode of claim 13 wherein the electrode body and the hydrogen generating cell are remotely positioned relative to each other, and wherein the electrode body and the hydrogen generating cell are operatively connected only by the conduit so that hydrogen produced by the hydrogen generating cell is supplied to the remotely positioned electrode body.

15. The measurement electrode of claim 13 which further includes an electrode body received by the first end of the conduit.

16. The measurement electrode of claim 15 wherein the electrode body is formed of a material having a catalytic capacity for chemisorptive cleavage of hydrogen molecules selected from the group consisting of Group VIII metals of the Periodic Table of Elements, alloys of such metals, and electron-conducting solids metallized with such metals and alloys of such metals.

17. The measurement electrode of claim 15 wherein the electrode body is retained over the first end of the conduit by an end cap for engaging the first end of the conduit, and for retaining the electrode body in electrical contact with the electrical connection.

18. The measurement electrode of claim 17 which further includes means for electrolytically separating the electrode body from an external test solution, in operative association with the end cap.

19. The measurement electrode of claim 13 which further includes a cell housing formed at the second end of the conduit, for receiving the hydrogen generating cell therein.

20. The measurement electrode of claim 19 wherein the cell housing further includes a sealing gasket positioned adjacent to the second end of the conduit, for engaging the hydrogen generating cell received within the cell housing.

21. The measurement electrode of claim 19 which further includes a cover for enclosing the cell housing so that the cell housing and the second end of the conduit with which it communicates are sealed, and for retaining the hydrogen generating cell within the cell housing.

22. The measurement electrode of claim 21 wherein the cover includes electrical contacts for electrical connection with the anode and the cathode of the hydrogen generating cell.

23. The measurement electrode of claim 22 wherein the electrical contacts are electrically connected with each other for operating the hydrogen generating cell.

24. The measurement electrode of claim 23 wherein the electrical contacts are electrically connected with each other by a resistor.

25. The measurement electrode of claim 24 wherein the electrical contacts are electrically connected by a potentiometer.

26. The measurement electrode of claim 25 wherein the potentiometer includes an on-off switch.

27. The measurement electrode of claim 23 wherein the electrical contacts are electrically connected with each other to develop a differential in voltage between the anode and the cathode of the hydrogen generating cell.

28. The measurement electrode of claim 27 wherein the differential in voltage is from 0 to 0.4 volts.

29. The measurement electrode of claim 22 wherein the electrical contacts provide spring means for placing the gas generating cell tightly against the second end of the conduit, for sealing engagement of the second end with the gas generating cell.

30. The measurement electrode of claim 22 wherein the electrical contacts extend to exterior portions of the cover, for connection with external monitoring means.

31. The measurement electrode of claim 21 wherein the cover includes spring means for placing the gas generating cell tightly against the second end of the conduit, for sealing engagement of the second end with the gas generating cell.

32. The measurement electrode of claim 31 wherein the cover is in snap-fit engagement with the cell housing.

33. The measurement electrode of claim 13 wherein the electrical connection extends through the conduit to a terminal fastened to the conduit and which is accessible from exterior portions of the conduit.

34. The measurement electrode of claim 13 which further includes a reservoir for containing a reference solution in communication with the conduit, and positioned along the conduit between the first end and the second end.

35. The measurement electrode of claim 34 wherein the reservoir further includes means for separating the reference solution and the hydrogen from each other.

36. The measurement electrode of claim 35 wherein the separating means is a capillary system for separately transporting the reference solution and the hydrogen.

37. The measurement electrode of claim 35 wherein the separating means is a porous system for separately transporting the reference solution and the hydrogen.

38. The measurement electrode of claim 34 which further includes a hydrogen generating cell received by the second end of the conduit, for providing hydrogen for interacting with the electrode body and for conveying the reference solution through the conduit.

39. The measurement electrode of claim 13 which further includes a hydrogen generating cell received by the second end of the conduit, including a cell housing having an aperture formed therein, and containing the anode, the cathode and an aqueous electrolyte, wherein the cathode is a hydrogen diffusing electrode for communicating with the aperture through a hydrophobic diffusion membrane.

40. The measurement electrode of claim 39 wherein the cathode includes a catalyst layer bound with polytetrafluoroethylene and rolled into a metal mesh, and a porous polytetrafluoroethylene foil covering the catalyst layer and the metal mesh.

41. The measurement electrode of claim 40 wherein the polytetrafluoroethylene foil lies on a side of the cathode which faces away from the anode.

42. The measurement electrode of claim 40 wherein the catalyst layer is Raney nickel.

43. The measurement electrode of claim 40 wherein the anode is zinc.

44. The measurement electrode of claim 43 wherein the electrolyte is potassium hydroxide.

* * * * *